United States Patent
Urbahns et al.

(12)

(10) Patent No.: US 6,194,428 B1
(45) Date of Patent: Feb. 27, 2001

(54) USE OF 5-SUBSTITUTED PYRIDINE AND HEXAHYDROQUINOLINE-3 CARBOXYLIC ACID DERIVATIVES FOR TREATING DISEASES OF THE CENTRAL NERVOUS SYSTEM

(75) Inventors: Klaus Urbahns, Wuppertal; Hans-Georg Heine, Krefeld; Bodo Junge; Rudolf Schohe-Loop, both of Wuppertal; Henning Sommermeyer, Köln; Thomas Glaser, Overath; Reilinde Wittka, Köln; Jean-Marie-Viktor de Vry, Rösrath, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/238,569

(22) Filed: Jan. 28, 1999

Related U.S. Application Data

(63) Continuation of application No. 08/793,793, filed as application No. PCT/EP95/03235 on Aug. 16, 1995, now abandoned.

(30) Foreign Application Priority Data

Aug. 29, 1994 (DE) ................................. 44 30 639

(51) Int. Cl.$^7$ .................. A61K 31/4355; A61K 31/437; A61K 31/47; C07D 471/04; C07D 491/04; A61P 25/18

(52) U.S. Cl. .................. 514/300; 514/302; 514/311; 514/314; 546/113; 546/116; 546/122; 546/167; 546/168

(58) Field of Search ................. 546/113, 116, 546/122, 168, 167; 514/300, 302, 311, 314

(56) References Cited

U.S. PATENT DOCUMENTS

| 4,264,611 | * | 4/1981 | Berntsson | 424/266 |
| 4,497,821 | | 2/1985 | Wehinger . | |
| 4,705,794 | | 11/1987 | Wehinger et al. . | |

FOREIGN PATENT DOCUMENTS

| 32 09 274 | 9/1983 | (DE) . |
| 32 09 276 | 9/1983 | (DE) . |

OTHER PUBLICATIONS

Goerelitzer et al., 'Anellated lactones from Bay–K–8644 . . . Hantzsch synthesis', Arch.Pharm.,vol. 324, No. 11, 1991, pp. 879–886.

S.–X. Wang et al., J.Pharmacol.Exp.Ther., vol. 250, No. 2, pp. 632–636 (1989).

C.Baäärnheilm et al., Drug Metabolism and Disposition, vol. 14, No. 5, pp. 613–618 (1986).

L. Weidolf et al., Acta Pharm. Suec., vol. 21, No. 6, pp. 331–344 (1984).

R. Nishioka et al., J.Chromatogr., vol. 565, pp. 237–246 (1991).

C. Bäärnhielm et al., Drug Metabolism and Disposition, vol. 14, No. 5, pp. 613–618 (1986).

* cited by examiner

Primary Examiner—Evelyn Mei Huang
(74) Attorney, Agent, or Firm—Norris McLaughlin & Marcus

(57) ABSTRACT

The invention relates to the use of 5-substituted pyridine- and hexahydroquinoline-3-carboxylic acid derivatives, some of which are known, for the production of medicaments, in particular for the treatment of cerebral disorders.

10 Claims, No Drawings

USE OF 5-SUBSTITUTED PYRIDINE AND HEXAHYDROQUINOLINE-3 CARBOXYLIC ACID DERIVATIVES FOR TREATING DISEASES OF THE CENTRAL NERVOUS SYSTEM

This application is a continuation of application Ser. No. 08/793,793, filed on Feb. 21, 1997 (now abandoned); which is a 371 of PCT/ET95/03235, filed on Aug. 16, 1995.

The present invention relates to the use of 5-substituted pyridine- and hexahydroquinoline-3-carboxylic acid derivatives for the production of medicaments, novel active compounds, a process for their preparation and their use, in particular as cerebrally active agents.

4-(2,3-Dichlorophenyl)-5,7-dihydro-2-methyl-5-oxoethyl furo[3,4-b]pyridine-3-carboxylate is already known from the publications J. Chromatogr., 565 (1–2), 237–46, 1991; J. Pharmacol. Exp. Ther. 250 (2), 632–6, 1989; Drug Metab. Dispos. 14 (5), 613–18, 1986 and Acta Pharm. Suec., 21 (6), 331–44, 1984.

It has now been found that the 5-substituted pyridine- and hexahydroquinoline-3-carboxylic acid derivatives of the general formula (I)

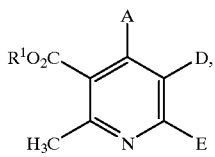
(I)

in which
  A represents aryl having 6 to 10 carbon atoms or pyridyl, each of which is optionally substituted up to 3 times by identical or different substituents from the group consisting of nitro, cyano, halogen and trifluoromethyl or straight-chain or branched alkyl, alkoxy or alkylthio having up to 6 carbon atoms,
  $R^1$ represents hydrogen or straight-chain or branched alkyl having up to 8 carbon atoms,
  D and E together represent —CO—O—CH$_2$—[CR$^2$R$^3$]$_a$—, —CO—NR$^4$—[CR$^2$R$^3$]$_a$—CH$_2$—, —CO—CH$_2$—[CR$^2$R$^3$]$_a$—CH$_2$— or

—CH$_2$—[CR$^2$R$^3$]$_a$—O—CO—, wherein
  $R^2$, $R^3$ and $R^4$ are identical or different and denote hydrogen or methyl,
  a denotes a number 0 or 1
  and their salts,
surprisingly have a modulating action on potassium channels and are thus suitable for the control of cerebral disorders.

In the context of the invention, physiologically acceptable salts are preferred. Physiologically acceptable salts are in general salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds according to the invention can exist in stereoisomeric forms which either behave as image and mirror image (enantiomers), or which do not behave as image and mirror image (diastereomers). The invention relates both to the antipodes and to the racemic forms as well as the diastereomer mixtures.

Preferably used are those compounds of the general formula (I) in which
  A represents phenyl, naphthyl or pyridyl, each of which is optionally substituted up to 3 times by identical or different substituents from the group consisting of nitro, cyano, fluorine, chlorine, bromine, iodine and trifluoromethyl or straight-chain or branched alkyl, alkoxy or alkylthio having up to 4 carbon atoms,
  $R^1$ represents hydrogen or straight-chain or branched alkyl having up to 6 carbon atoms,
  D and E together represent —CO—O—CH$_2$—[CR$^2$R$^3$]$_a$—, —CO—NR$^4$—[CR$^2$R$^3$]$_a$—CH$_2$—, —CO—CH$_2$—[CR$^2$R$^3$]$_a$—CH$_2$— or

—CH$_2$—[CR$^2$R$^3$]$_a$—O—CO—, wherein
  $R^2$, $R^3$ and $R^4$ are identical or different and denote hydrogen or methyl,
  a denotes a number 0 or 1,
  and their salts,
in the control of cerebral disorders.

Particularly preferably used are those compounds of the general formula (I) in which
  A represents phenyl or pyridyl, each of which is optionally substituted up to 2 times by identical or different substituents from the group consisting of nitro, cyano, fluorine, chlorine, bromine, iodine and trifluoromethyl or methyl, methoxy or methylthio,
  $R^1$ represents hydrogen or straight-chain or branched alkyl having up to 4 carbon atoms,
  D and E together represent —CO—O—CH$_2$—[CR$^2$R$^3$]$_a$—, —CO—NR$^4$—[CR$^2$R$^3$]$_a$—CH$_2$—, —CO—CH$_2$—[CR$^2$R$^3$]$_a$—CH$_2$— or

—CH$_2$—[CR$^2$R$^3$]$_a$—O—CO—, wherein
  $R^2$, $R^3$ and $R^4$ are identical or different and denote hydrogen or methyl,
  a denotes a number 0 or 1,
  and their salts,
in the control of cerebral disorders.

The compounds of the general formula (I) according to the invention show an unforeseeable, useful spectrum of pharmacological action.

They are modulators of channels having selectivity for calcium-dependent potassium channels of high conductivity (BK(Ca) channels), in particular of the central nervous system.

On account of their pharmacological properties, they can be employed for the production of medicaments for the treatment of degenerative central nervous system disorders, such as e.g. on occurrence of dementias such as multiinfarct dementia (MID), primary degenerative dementia (PDD), presenile and senile dementia of the Alzheimer's disease type, HIV dementia and other forms of dementia, and also for the treatment of Parkinson's disease or amyotrophic lateral sclerosis and also multiple sclerosis.

The active compounds are furthermore suitable for the treatment of brain function disorders in old age, of organic brain syndrome (OBS) and of age-related memory disorders (age-associated memory impairment, AAMI).

They are suitable for the prophylaxis, for the treatment and for the control of the sequelae of cerebral circulatory disorders such as cerebral ischaemias, strokes, craniocerebral traumata and subarachnoid haemorrhages.

They are useful for the treatment of depressions and psychoses, e.g. schizophrenia. They are additionally suitable for the treatment of disorders of neuroendocrine secretion and of neurotransmitter secretion and health disorders connected therewith such as mania, alcoholism, drug abuse, dependence or abnormal eating behaviour. Other application areas are the treatment of migraine, sleep disorders and neuropathies. They are moreover suitable as analgaesics.

The active compounds are further suitable for the treatment of disorders of the immune system, in particular of T-lymphocyte proliferation and for affecting the smooth musculature, in particular of uterus, urinary bladder and bronchial tract and for the treatment of diseases connected therewith such as e.g. asthma and urinary incontinence and for the treatment of high blood pressure, arrhythmia, angina and diabetes.

The invention additionally relates to new compounds of the general formula (Ia)

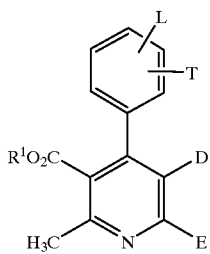

(Ia)

and their salts, having the substituent meanings indicated in the following table:

| $R^1$ | L | T | D–E |
|---|---|---|---|
| —CH$_3$ | 4-Cl | H | —CO—O—CH$_2$— |
| —CH(CH$_3$)$_2$ | 4-Cl | H | —CO—O—CH$_2$— |
| —CH(CH$_3$)$_2$ | 2-Cl | 3-Cl | —CO—O—CH$_2$— |
| —CH$_3$ | 4-Cl | H | —CO—NH—CH$_2$— |

-continued

| $R^1$ | L | T | D–E |
|---|---|---|---|
| —CH(CH$_3$)$_2$ | 4-Cl | H | —CO—NH—CH$_2$— |
| —CH$_3$ | 2-Cl | 3-Cl | —CO—NH—CH$_2$— |
| —CH(CH$_3$)$_2$ | 2-Cl | 3-Cl | —CO—NH—CH$_2$— |
| —CH$_3$ | 4-Cl | H | —CO—CH$_2$—CH$_2$—CH$_2$— |
| —CH(CH$_3$)$_2$ | 4-Cl | H | —CO—CH$_2$—CH$_2$—CH$_2$— |
| —CH$_3$ | 2-Cl | 3-Cl | —CO—CH$_2$—CH$_2$—CH$_2$— |
| —CH(CH$_3$)$_2$ | 2-Cl | 3-Cl | —CO—CH$_2$—CH$_2$—CH$_2$— |
| —CH(CH$_3$)$_2$ | 2-Cl | 3-Cl | —CO—CH$_2$—C(CH$_3$)$_2$—CH$_2$— |
| —CH$_3$ | 3-H | 4-Cl | —CO—CH$_2$—C(CH$_3$)$_2$—CH$_2$— |
| —CH$_3$ | 2-Cl | 3-Cl | —CO—CH$_2$—C(CH$_3$)$_2$—CH$_2$— |
| —CH(CH$_3$)$_2$ | 3-Cl | 4-Cl | —CO—O—CH$_2$— |
| —CH$_3$ | 2-F | 3-F | —CO—O—CH$_2$— |
| —CH$_3$ | 4-F | 3-H | —CO—O—CH$_2$— |
| —CH$_3$ | 2-F | 6-Cl | —CO—O—CH$_2$— |
| —CH$_3$ | 3-H | 4-Cl | —CH$_2$—O—CO— |
| —CH(CH$_3$)$_2$ | 2-Cl | 3-Cl | —CH$_2$—O—CO— |
| —CH(CH$_3$)$_2$ | 3-H | 4-Cl | —CH$_2$—O—CO— |
| —CH$_3$ | 2-Cl | 3-Cl | —CH$_2$—O—CO— |

The compounds of the general formulae (I) and (Ia) are prepared by

[A] in the case where D and E together represent —CO—NR$^4$—[CR$^2$R$^3$]$_a$—CH$_2$—, oxidizing the dihydropyridines of the formula (II)

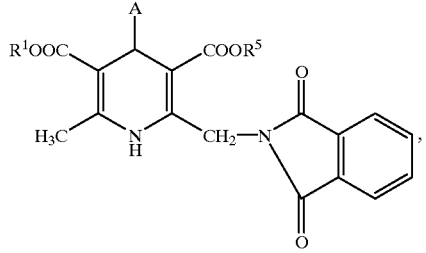

(II)

wherein $R^1$ and A have the meaning indicated and $R^5$ represents C$_1$–C$_4$-alkyl, in inert solvents to give the corresponding pyridine and then closing this with hydrazine hydrate to give the lactam and optionally alkylating the nitrogen, or

[B] in the case where D and E together represent —CO—O—CH$_2$—[CR$^2$R$^3$]$_a$—, —CO—CH$_2$—[CR$^2$R$^3$]$_a$—CH$_2$— or —CH$_2$—[CR$^2$R$^3$]$_a$—O—CO, oxidizing the corresponding dihydropyridines.

The processes according to the invention can be illustrated by way of example by the following equations:

[A]
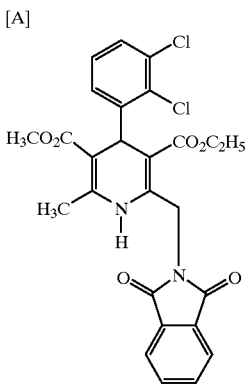

↓ $N_2H_4 \times H_2O$

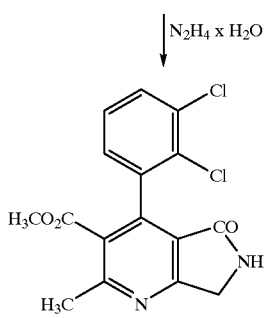

[B]
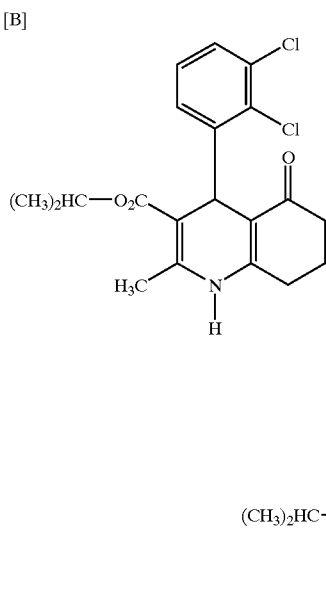

Suitable solvents for the process here are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether, acetonitrile, or amides such as hexamethylphosphoramide or dimethylformamide, or acetic acid or halogenated hydrocarbons such as methylene chloride or carbon tetrachloride, or hydrocarbons such as benzene or toluene. It is also possible to use mixtures of the solvents mentioned. Isopropanol, ethanol, tetrahydrofuran, methanol, methylene chloride and dimethylformamide are particularly preferred.

Suitable oxidizing agents are in general 2,3-dichloro-4,5-dicyano-p-benzoquinone and derivatives, pyridinium dichromate, elemental bromine or iodine and manganese dioxide. Manganese dioxide is preferred.

The oxidizing agent is in general employed in an amount from 1 mol to 20 mol, preferably from 1 mol to 5 mol, in each case relative to 1 mol of the dihydropyridines. In the case of $MnO_2$, a 5- to 20-fold amount by weight is added.

Suitable solvents for the oxidation are the abovementioned solvents, methylene chloride being preferred.

The reaction temperatures can be varied within a relatively wide range. In general, the reaction is carried out between +10° C. and +150° C., preferably between +20° C. and +100° C., in particular at room temperature.

The reactions can be carried out at normal pressure, but also at elevated or reduced pressure (e.g. 0.5 to 3 bar). In general the reactions are carried out at normal pressure.

The hydrolysis of the carboxylic acid esters is carried out according to customary methods, by treating the esters in inert solvents with customary bases.

The reaction with hydrazine hydrate and the alkylation are carried out according to customary methods.

[86]Rubidium Efflux from C6-BU1 Glioma Cells

The experiments were carried out with slight modifications corresponding to the method described by Tas et al. (Neurosci. Lett. 94, 279–284, (1988)). To do this, rat C6-BU1 glioma cells are used. From the data obtained by liquid scintillation, the increase in Rb efflux produced by ionomycin above the basal efflux is calculated and set as 100%. The stimulations in the presence of test substances are then related to this value.

The present invention also includes pharmaceutical preparations which, in addition to inert, non-toxic, pharmaceutically suitable auxiliaries and excipients, contain one or more compounds of the general formulae (I)/(Ia), or which consist of one or more active compounds of the formulae (I) and (Ia), and processes for the production of these preparations.

The active compounds of the formulae (I)/(Ia) should be present in these preparations in a concentration of 0.1 to 99.5% by weight, preferably of 0.5 to 95% by weight of the total mixture.

In addition to the active compounds of the formulae (I)/(Ia), the pharmaceutical preparations can also contain other pharmaceutical active compounds.

The abovementioned pharmaceutical preparations can be prepared in a customary manner according to known methods, for example using the auxiliary(ies) or excipient(s).

In general, it has proven advantageous to administer the active compound(s) of the formulae (I)/(Ia) in total amounts from about 0.01 to about 100 mg/kg, preferably in total amounts from about 1 mg/kg to 50 mg/kg of body weight every 24 hours, if appropriate in the form of several individual doses, to achieve the desired result.

However, if appropriate it may be advantageous to depart from the amounts mentioned, namely depending on the nature and on the body weight of the subject treated, on individual behaviour towards the medicament, the nature and severity of the disorder, the type of preparation and administration, and the time or interval at which administration takes place.

Mobile Phase Mixtures a: methylene chloride/AcOEt 10+1
b: methylene chloride/MeOH 10+1
c: PE/AcOEt 7+3
d: PE/AcOEt 1+1

Starting Compounds

EXAMPLE I

Methyl 1,4,5,7-tetrahydro-4-(4-chlorophenyl)-2-methyl-5-oxo-furo[3,4-b]-pyridine-3-carboxylate

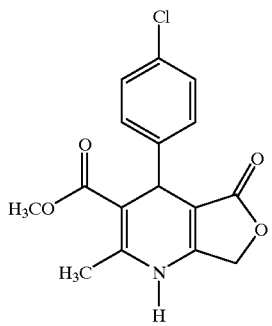

3 g (21.3 mmol) of 4-chlorobenzaldehyde, 4.0 g (21.3 mmol) of ethyl 4-acetoxyacetoacetate and 2.5 g (21.3 mmol) of methyl 3-aminocrotonate are dissolved in 40 ml of isopropanol and heated to reflux for 12 h. The mixture is then treated with 10 ml of dilute aqueous HCl and heated to reflux for a further 30 min. The mixture is partitioned between toluene and water. Drying (MgSO$_4$) and concentration of the organic phase yields a white solid which is purified by filtration through 50 g of silica gel (ethyl acetate/petroleum ether 1+1) and subsequent recrystallization from ethyl acetate/petroleum ether. 2.6 g (8.13 mmol, 38%) are obtained.

EXAMPLE II 4-(2,3-Dichlorophenyl)-3-ethoxycarbonyl-5-methoxycarbonyl-6-methyl-2-phthalimidomethyl-1,4-dihydropyridine

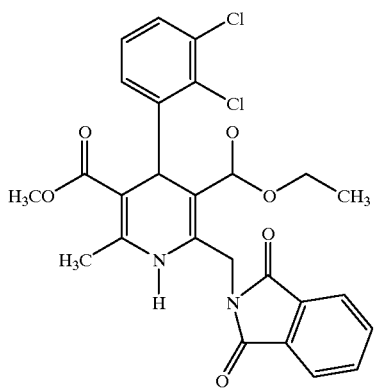

4.4 g (25 mmol) of 2,3-dichlorobenzaldehyde, 6.9 g (25 mmol) of ethyl 4-N-phthalimido-3-oxobutanoate and 2.9 g (25 mmol) of methyl 3-aminocrotonate are dissolved in 25 ml of abs. ethanol and heated to reflux for 12 h. The product partially precipitates on cooling to RT. The precipitation is completed by addition of 50 ml of petroleum ether. The solid is filtered off with suction and washed with ether. Yield 4.79 g.

EXAMPLE III 4-(2,3-Dichlorophenyl)-3-ethoxycarbonyl-5-methoxycarbonyl-6-methyl-2-phthalimidomethylpyridine

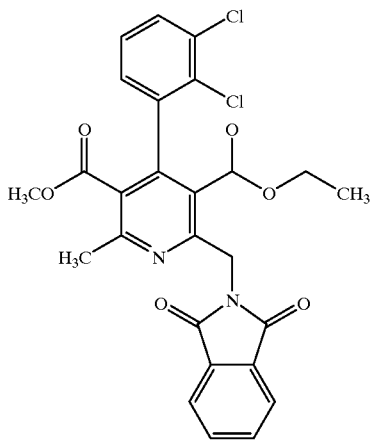

Analogously to the procedure for Example I, 2.3 g (4.3 mmol) of the compound from Example II are oxidized by 10 g of manganese dioxide at RT for 1 h to give 2.0 g (88% of theory) of the title compound.

EXAMPLE IV

Isopropyl 4-(2,3-dichlorophenyl)-2-methyl-5-oxo-1,4,5,6,7,8-hexahydroquinoline-3-carboxylate

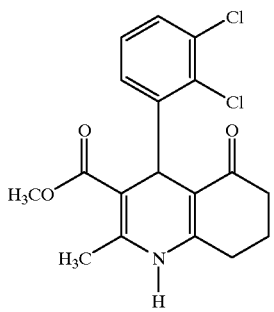

3.50 g (20 mmol) of 2,3-dichlorobenzaldehyde, 2.24 g (20 mmol) of dihydroresorcinol and 2.86 g (20 mmol) of isopropyl 3-aminocrotonate are dissolved in 100 ml of isopropanol and stirred under reflux for 5 h. The product precipitates. The mixture is treated with 50 ml of water and cooled to RT. The product is filtered off with suction and washed successively with isopropanol, ethanol and ether. 5.8 g (74% of theory) of the title compound are obtained.

EXAMPLE V

Isopropyl 4-(2,3-dichlorophenyl)-5-oxo-2,7,7-trimethyl-1,4,5,6,7,8-hexa-hydroquinoline-3-carboxylate

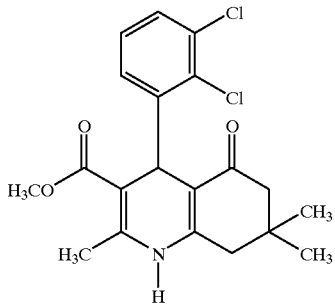

3.50 g (20 mmol) of 2,3-dichlorobenzaldehyde, 2.80 g (20 mmol) of dimedone and 2.86 g (20 mmol) of isopropyl 3-aminocrotonate are dissolved in 100 ml of isopropanol and stirred under reflux for 5 h. The product precipitates. The mixture is treated with 50 ml of water and cooled to RT. The product is filtered off with suction and washed successively with isopropanol, ethanol and ether. 6.6 g (78% of theory) of the title compound are obtained.

EXAMPLE VI

2-Azido-γ-butyrolactone

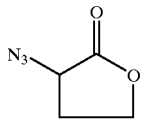

1.56 g (10 mmol) of 2-bromo-γ-butyrolactone are dissolved in 2 ml of dimethylformamide and treated at 0° C. with 612 mg (12.5 mmol) of lithium azide. The mixture is stirred at room temperature for 2 h, treated with water and extracted three times with methylene chloride. The combined organic phases are washed three times with water, dried over sodium sulphate and concentrated. 1.10 g (86.6% of theory) of the title compound are obtained.

MS: 127

EXAMPLE VII

2-Amino-γ-but-2-en-yrolactone

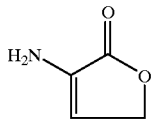

1.02 g (0.8 mmol) of the compound from Example VI in 2 ml of ethanol are added dropwise at 20° C. to a solution of 50 g of sodium in 5 ml of ethanol. The mixture is stirred at room temperature for 30 min and concentrated under reduced pressure. The precipitated solid is stirred in a little cold ethanol and the residue is dissolved in hot ethyl acetate. The solution is filtered and concentrated. 350 mg (44% of theory) of colourless solid are obtained.

MS: 99

EXAMPLE VIII

Isopropyl 1,4,5,7-tetrahydro-4-(4-chlorophenyl)-2-methyl-7-oxo-furo[3,4-b]pyridine-3-carboxylate

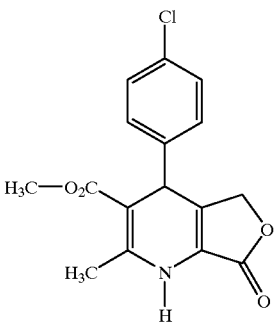

9.0 g (30 mmol) of isopropyl 2,3-dichlorobenzylideneacetoacetate and 3.0 g (30 mmol) of the compound 2-amino-γ-but-2-en-yrolactone are dissolved in 60 ml of isopropanol and treated with 1.7 ml (30 mmol) of AcOH. The mixture is kept under reflux for 20 h. It is then concentrated and the residue is purified on 100 g of silica gel 60 (ethyl acetate/petroleum ether 10:1, then 5:1). The resulting material is recrystallized from ether. 4.08 g (36% of theory) of the title compound are obtained.

MS: 381

Preparation Examples

Example 1

Methyl 5,7-dihydro-4-(4-chlorophenyl)-2-methyl-5-oxo-furo[3,4-b]-pyridine-3-carboxylate

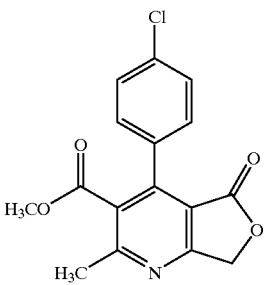

Analogously to Example 3, the title compound is obtained in 1.01 g (76% of theory) yield from 1.33 g (4.16 mmol) of methyl 1,4,5,7-tetrahydro-4-(4-chlorophenyl)-2-methyl-5-oxo-furo[3,4-b]-pyridine-3-carboxylate by oxidation with $MnO_2$ in $CH_2Cl_2$.

Example 2

Methyl 5,7-dihydro-4-(2,3-dichlorophenyl)-2-methyl-5-oxo-pyrrolo-[3,4-b]-pyridine-3-carboxylate

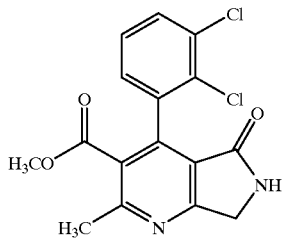

1.9 g (3.6 mmol) of the compound from Example III are suspended in 100 ml of ethanol and treated with 0.5 ml (10 mmol) of hydrazine hydrate. After stirring at RT for 30 min a clear solution is formed. After reflux for 30 min a white precipitate is deposited. The mixture is allowed to cool and the precipitate is filtered off with suction. The solid is purified by chromatography (methylene chloride/ethyl acetate 20+1) and finally recrystallized from ethanol. 0.56 g (44%) is obtained.

Example 3

Isopropyl 4-(2,3-dichlorophenyl)-2-methyl-5-oxo-5,6,7,8-tetrahydroquinoline-3-carboxylate

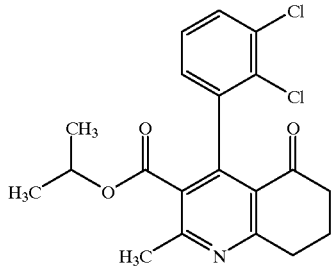

1.5 g (3.8 mmol) of the compound from Example IV are dissolved in 350 ml of $CH_2Cl_2$ and treated with 7.5 g of $MnO_2$. The mixture is kept under reflux for 2 h, solid is filtered off with suction through Celite and the filtrate is concentrated. The residue is purified by MPLC (methylene chloride/ethyl acetate 10+1). After recrystallization, first from ether/petroleum ether and then from isopropanol/petroleum ether, 0.72 g (48% of theory) of the title compound is obtained.

MS: 391

Example 4

Isopropyl 4-(2,3-dichlorophenyl)-2,7,7-trimethyl-5-oxo-5,6,7,8-tetrahydroquinoline-3-carboxylate

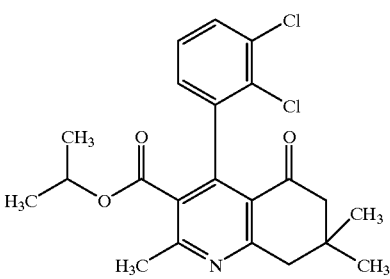

1.6 g (3.8 mmol) of the compound from Example V are dissolved in 350 ml of $CH_2Cl_2$ and treated with 7.5 g of $MnO_2$. The mixture is kept under reflux for 2 h, solid is filtered off with suction through Celite and the filtrate is concentrated. The residue crystallizes from ether/petroleum ether. 1.1 g (69% of theory) of the title compound are obtained.

MS: 419

The compounds listed in Tables 1, 2 and 3 are prepared in analogy to the preparation processes described above:

TABLE 1

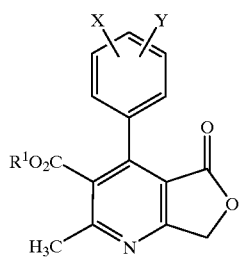

| Ex. No. | X, Y | $R^1$ | Yield (% of theory) | $R_f$*/m.p. (° C.) | MS |
|---|---|---|---|---|---|
| 5 | 4-Cl/H | —CH(CH$_3$)$_2$ | 78 | 0.45/d | 345 |
| 6 | 2-Cl, 3-Cl | —CH(CH$_3$)$_2$ | 87 | 199–200 | 379 |
| 7 | 3-Cl, 4-Cl | —CH(CH$_3$)$_2$ | 60 | 0.42/a | 379 |
| 8 | 2-F, 3-F | —CH$_3$ | 65 | 0.45/a | 319 |
| 9 | 4-F/H | —CH$_3$ | 39 | 0.34/a | 301 |
| 10 | 2-Cl, 6-F | —CH$_3$ | 13 | 0.57/a | 335 |
| 11 | 2-Cl, 3-Cl | —CH(CH$_3$)$_2$ | 47 | 0.24/b | 378 |

TABLE 2

| Ex. No. | X, Y | $R^1$ | Yield (% of theory) | $R_f^*$/ | MS |
|---|---|---|---|---|---|
| 12 | 4-Cl | —$CH_3$ | 47 | 0.45/a | 329 |
| 13 | 4-Cl | —$CH(CH_3)_2$ | 81 | 0.34/a | 357 |
| 14 | 2-Cl, 3-Cl | —$CH_3$ | 38 | 0.52/a | 363 |

TABLE 3

| Ex. No. | X/Y | Yield (% of theory) | $R_f^*$ |
|---|---|---|---|
| 15 | 4-Cl/H | 73 | 0.67/a |
| 16 | 2-Cl, 3-Cl | 65 | 0.71/a |

Example 17

Methyl 5,7-dihydro-4-(4-chlorophenyl)-2-methyl-7-oxo-furo [3,4-b]-pyridine-3-carboxylate

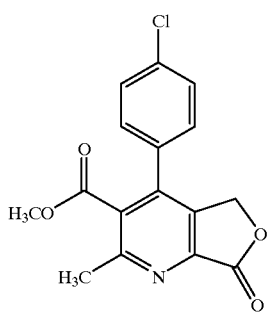

Corresponding to Example 1, 1.5 g (3.92 mmol) of methyl 1,4,5,7-tetrahydro-4-(4-chlorophenyl)-2-methyl-7-oxo-furo [3,4-b]-pyridine-3-carboxylate in 350 ml of methylene chloride are reacted with 7.5 g of manganese dioxide to give 0.94 g (63% of theory) of the title compound.

MS: 380

$R_f$=0.57 (methylene chloride/ethyl acetate 10+1)

The compounds listed in Table 4 are prepared in analogy to the procedure of Example 17:

TABLE 4

| Ex. No. | X/Y | $R^{1'}$ | Yield (% of theory) | $R_f^*$ |
|---|---|---|---|---|
| 18 | 2-Cl, 3-Cl | —$CH(CH_3)_2$ | 36 | 0.57/c |
| 19 | 4-Cl/H | —$CH(CH_3)_2$ | 67 | 0.48/c |
| 20 | 2-Cl, 3-Cl | —$CH_3$ | 72 | 0.29/c |

The compounds listed in Table 5 are prepared in analogy to the produce of Example 2:

TABLE 5

| Ex. No. | X/Y | $R^{1'}$ | Yield (% of theory) | $R_f^*$ | MS |
|---|---|---|---|---|---|
| 21 | 4-Cl/H | —$CH_3$ | 51 | 0.20/b | 316 |
| 22 | 4-Cl/H | —$CH(CH_3)_2$ | 22 | 0.21/b | 344 |

What is claimed is:

1. A compound selected from the group of:

Isopropyl 5,7-dihydro-4-(2,3-dichlorophenyl)-2-methyl-5-oxo-furo[3,4-b]-pyridine-3-carboxylate,
Isopropyl 5,7-dihydro-4-(3,4-dichlorophenyl)-2-methyl-5-oxo-furo[3,4-b]-pyridine-3-carboxylate,
Methyl5,7-dihydro-4-(2,3-difluorophenyl)-2-methyl-5-oxo-furo[3,4-b]-pyridine-3-carboxylate, and
Methyl 5,7-dihydro-4-(2-chloro-6-fluoro-phenyl)-2-methyl-5-oxo-furo[3,4-b]-pyridine-3-carboxylate.

2. A method of treating depression or psychosis which comprises administering to a host in need thereof an effective amount of a compound of the formula

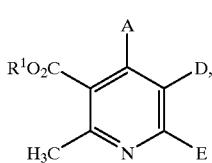

(I)

in which

A represents phenyl which is substituted 2 times by identical or different substituents selected from the group consisting of fluorine, chlorine, bromine, and iodine, $R^1$ represents hydrogen or straight-chain or branched alkyl having up to 4 carbon atoms, D and E together represent —CO—O—CH$_2$—[CR$^2$R$^3$]$_a$—, wherein $R^2$ and $R^3$ are identical or different and denote hydrogen or methyl, a denotes a number 0 or 1, or a salt thereof.

3. A method of treating depression or psychosis which comprises administering to a host in need thereof an effective amount of a compound of the formula

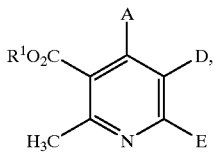

(I)

in which

A represents phenyl which is optionally substituted up to 2 times by identical or different substituents selected from the group consisting of fluorine, chlorine, bromine, and iodine, $R^1$ represents hydrogen or straight-chain or branched alkyl having up to 4 carbon atoms, D and E together represent —CO—NR$^4$—[CR$^2$R$^3$]$_a$—CH$_2$—, —CO—CH$_2$—[CR$^2$R$^3$]$_a$—CH$_2$— or

—CH$_2$—[CR$^2$R$^3$]$_a$—O—CO—, wherein $R^2$, $R^3$ and $R^4$ are identical or different and denote hydrogen or methyl, a denotes a number 0 or 1, or a salt thereof.

4. A composition comprising at least one compound according to claim 1 and an auxiliary or excipient.

5. A process for the preparation of the compound according to claim 1, wherein the corresponding dihydropyridine is oxidized.

6. A method of treating depression or psychosis which comprises administering an effective amount of a compound according to claim 1, to a host in need thereof.

7. A compound selected from the group consisting of:

Methyl 5,7-dihydro-4-(2,3-dichlorophenyl)-2-methyl-5-oxo-pyrrolo[3,4-b]-pyridine-3-carboxylate,
Isopropyl 4-(2,3-dichlorophenyl)-2-methyl-5-oxo-5,6,7,8-tetrahydroquinoline-3-carboxylate,
Isopropyl 4-(2,3-dichlorophenyl)-2,7,7-trimethyl-5-oxo-5,6,7,8-tetrahydroquinoline-3-carboxylate,
Methyl 5,7-dihydro-4-(4-chlorophenyl)-2-methyl-5-oxo-pyrrolo[3,4-b]-pyridine-3-carboxylate,
Isopropyl 5,7-dihydro-4-(4-chlorophenyl)-2-methyl-5-oxo-pyrrolo[3,4-b]-pyridine-3-carboxylate,
Isopropyl 5,7-dihydro4-(2,3-dichlorophenyl)-2-methyl-5-oxo-pyrrolo[3,4-b]-pyridine-3-carboxylate,
Methyl 4-(3,4-dichlorophenyl)-2-methyl-5-oxo-5,6,7,8-tetrahydroquinoline-3-carboxylate,
Isopropyl 4-(3,4-dichlorophenyl)-2-methyl-5-oxo-5,6,7,8-tetrahydroquinoline-3-carboxylate,
Methyl 4-(2,3-dichlorophenyl)-2-methyl-5-oxo-5,6,7,8-tetrahydroquinoline-3-carboxylate,
Methyl 4-(4-chlorophenyl)-2,7,7-trimethyl-5-oxo-5,6,7,8-tetrahydroquinoline-3-carboxylate,
Methyl 4-(2,3-dichlorophenyl)-2,7,7-trimethyl-5-oxo-5,6,7,8-tetrahydroquinoline-3-carboxylate,
Isopropyl 5,7-dihydro-4-(2,3-dichlorophenyl)-2-methyl-7-oxo-furo[3,4-b]-pyridine-3-carboxylate,
Methyl 5,7-dihydro-4-(4-chlorophenyl)-2-methyl-7-oxo-furo[3,4-b]-pyridine-3-carboxylate,
Methyl 5,7-dihydro-4-(2,3-dichlorophenyl)-2-methyl-7-oxo-furo[3,4-b]-pyridine-3-carboxylate, and
Isopropyl 5,7-dihydro-4-(4-chlorophenyl)-2-methyl-7-oxo-furo[3,4-b]-pyridine-3-carboxylate.

8. A composition comprising at least one compound according to claim 7 and an auxiliary or excipient.

9. A process for the preparation of compounds according to claim 7, wherein the corresponding dihydropyridine is oxidized.

10. A method of treating depression or psychosis which comprises administering an effective amount of a composition according to claim 8, to a host in need thereof.

* * * * *